(12) United States Patent
Yu et al.

(10) Patent No.: US 12,023,141 B2
(45) Date of Patent: Jul. 2, 2024

(54) SYSTEMS FOR MONITORING MICROCIRCULATION

(71) Applicants: RUIJIN HOSPITAL, SHANGHAI JIAO TONG UNIVERSITY SCHOOL OF MEDICINE, Shanghai (CN); SHANGHAI JIAO TONG UNIVERSITY, Shanghai (CN)

(72) Inventors: Buwei Yu, Shanghai (CN); Chongzhao Wu, Shanghai (CN); Han Lu, Shanghai (CN); Xiaomei Chi, Shanghai (CN); Bo Chen, Shanghai (CN)

(73) Assignees: RUIJIN HOSPITAL, SHANGHAI JIAO TONG UNIVERSITY SCHOOL OF MEDICINE, Shanghai (CN); SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 18/300,364

(22) Filed: Apr. 13, 2023

(65) Prior Publication Data
US 2023/0248254 A1 Aug. 10, 2023

Related U.S. Application Data

(63) Continuation of application No. PCT/CN2021/128815, filed on Nov. 4, 2021.

(30) Foreign Application Priority Data

Nov. 4, 2020 (CN) .......................... 202011218035.4

(51) Int. Cl.
*A61B 5/00* (2006.01)
*A61B 5/026* (2006.01)

(52) U.S. Cl.
CPC ............ *A61B 5/0261* (2013.01); *A61B 5/682* (2013.01); *A61B 5/6838* (2013.01);
(Continued)

(58) Field of Classification Search
CPC ..... A61B 5/0261; A61B 5/682; A61B 5/6838; A61B 5/6843; A61B 2562/0247; A61B 2562/168
See application file for complete search history.

(56) References Cited

U.S. PATENT DOCUMENTS 6,055,447 A 4/2000 Weil et al.
2008/0267232 A1* 10/2008 DeNatale ................. G04F 5/14
372/27
(Continued)

FOREIGN PATENT DOCUMENTS

CN 103622674 A 3/2014
CN 205251518 U 5/2016
(Continued)

OTHER PUBLICATIONS

International Search Report in PCT/CN2021/128815 mailed on Jan. 26, 2022, 7 pages.
(Continued)

*Primary Examiner* — Serkan Akar
*Assistant Examiner* — Amal Aly Farag
(74) *Attorney, Agent, or Firm* — METIS IP LLC (57) ABSTRACT

The present disclosure is related to a system for monitoring microcirculation. The system may include a detector, a light source, and a lens set. The detector is inserted under a tongue of a user along a sagittal axis direction of the user; the light source is disposed on a surface of the detector in contact with a bottom surface of the tongue of the user and is configured to emit a light source signal to a target region under the tongue; and the lens set is disposed within the
(Continued)

detector for receiving a detection signal from the target region. The detection signal is emitted into the detector along a vertical axis direction of the user and emitted out from the detector along the sagittal axis direction of the user.

20 Claims, 4 Drawing Sheets (52) U.S. Cl.
CPC .... *A61B 5/6843* (2013.01); *A61B 2562/0247* (2013.01); *A61B 2562/168* (2013.01)

(56) References Cited

U.S. PATENT DOCUMENTS

| | | | |
|---|---|---|---|
| 2010/0141829 | A1 | 6/2010 | Jalali et al. |
| 2011/0160595 | A1* | 6/2011 | Stone ................ A61B 5/0075 600/475 |
| 2012/0265039 | A1 | 10/2012 | Kiani |
| 2013/0184555 | A1 | 7/2013 | Chen et al. |
| 2013/0189641 | A1* | 7/2013 | Perfect ................ A61B 1/247 433/29 |
| 2016/0320531 | A1* | 11/2016 | Kamali ................ G02B 1/002 |
| 2018/0116585 | A1 | 5/2018 | Jing |
| 2018/0184917 | A1 | 7/2018 | Kiani |
| 2018/0296098 | A1 | 10/2018 | Islam |
| 2018/0368936 | A1* | 12/2018 | Habeb ................ A61C 1/082 |
| 2019/0046302 | A1* | 2/2019 | Li ................ A61B 5/4547 |
| 2019/0154877 | A1 | 5/2019 | Capasso et al. |
| 2019/0357761 | A1 | 11/2019 | Hessler et al. |
| 2021/0322767 | A1 | 10/2021 | Kent et al. |
| 2022/0039772 | A1 | 2/2022 | Jiang et al. |

FOREIGN PATENT DOCUMENTS

| | | |
|---|---|---|
| CN | 105832304 A | 8/2016 |
| CN | 107854116 A | 3/2018 |
| CN | 108852300 A | 11/2018 |
| CN | 109124588 A | 1/2019 |
| CN | 109283685 A | 1/2019 |
| CN | 109343217 A | 2/2019 |
| CN | 109363663 A | 2/2019 |
| CN | 109799611 A | 5/2019 |
| CN | 111426381 A | 7/2020 |
| CN | 111568355 A | 8/2020 |
| CN | 111624688 A | 9/2020 |
| CN | 112336309 A | 2/2021 |
| CN | 112353378 A | 2/2021 |
| CN | 112353379 A | 2/2021 |
| CN | 213721920 U | 7/2021 |
| JP | 2016087299 A | 5/2016 |
| WO | 2018185056 A1 | 10/2018 |

OTHER PUBLICATIONS

First Office Action in Chinese Application No. 202011218035.4 mailed on May 26, 2021, 18 pages.

\* cited by examiner

SYSTEMS FOR MONITORING MICROCIRCULATION

CROSS-REFERENCE TO RELATED APPLICATIONS

This application is a continuation of International Application No. PCT/CN2021/128815, filed on Nov. 4, 2021, which claims priority of Chinese Patent Application No. 202011218035.4, filed on Nov. 4, 2020, the contents of which are hereby incorporated by reference.

TECHNICAL FIELD

This disclosure generally relates to microcirculation technology, and more particularly, relates to systems for monitoring microcirculation.

BACKGROUND

Monitoring microcirculation under a tongue is increasingly important in clinical applications due to its convenience and non-invasive nature. Existing microcirculation monitoring systems usually require an operator to hold a detector. Due to the unavoidable physiological shaking of the operator, it is difficult to obtain a stable image. It is also difficult for the operator to hold the detector for a long time for continuous monitoring. Also, the detector's compression on the tongue may affect the blood flow rate and even injure the tongue. Therefore, it is desirable to provide systems for monitoring microcirculation that can achieve continuous and accurate monitoring without hand-holding and without compressing the tongue.

SUMMARY

In an aspect of the present disclosure, a system for monitoring microcirculation is provided. The system may include a detector, the detector being inserted under a tongue of a user along a sagittal axis direction of the user; a light source, the light source being disposed on a surface of the detector in contact with a bottom surface of the tongue of the user and being configured to emit a light source signal to a target region under the tongue; and a lens set, the lens set being disposed within the detector for receiving a detection signal from the target region, wherein the detection signal is emitted into the detector along a vertical axis direction of the user and emitted out from the detector along the sagittal axis direction of the user.

In some embodiments, the system may further include a hook connected to the detector, the hook being hung on a tooth or a gum of the user for fixing the detector.

In some embodiments, one end of the hook is optically coupled to a detection signal output terminal of the detector for receiving the detection signal; and a flexible optical fiber is disposed within the hook along an extension direction of the hook for transmitting the detection signal.

In some embodiments, the system may further include a processor, the processor being connected to the other end of the hook for receiving and processing the detection signal to generate a microcirculation image of the target region.

In some embodiments, a material of the hook is a flexible material.

In some embodiments, the system may further include a processor, the processor being wirelessly connected to the detector for receiving and processing the detection signal to generate a microcirculation image of the target region.

In some embodiments, the lens set includes a microlens for converging the detection signal of the target region.

In some embodiments, the microlens is a metasurface-based microlens.

In some embodiments, the metasurface-based microlens includes a metasurface unit array, the metasurface unit array including a plurality of media bins or a plurality of media columns.

In some embodiments, the metasurface unit array is internally integrated with a battery resonance element for performing a phase compensation on the detection signal.

In some embodiments, the lens set further includes a reflector, the reflector being configured that the detection signal is emitted into the detector along a vertical axis direction of the user and emitted out of from the detector along the sagittal axis direction of the user.

In some embodiments, the system may further include a sleeve for accommodating the detector.

In some embodiments, a shape of the sleeve is matched to a shape of the detector.

In some embodiments, a surface of the sleeve is a rounded curved surface of a bionic tongue.

In some embodiments, the sleeve is disposed with a snap-on structure for installing or removing the sleeve.

In some embodiments, the detector includes an optical isolation zone for blocking the light source signal or a reflected signal of the light source signal from emitting into the detector, the optical isolation zone is close to a side of the detector near the of the detector in contact with the bottom surface of the tongue.

In some embodiments, the system may further include a pressure measuring conduit, the pressure measuring conduit being filled with fluid and disposed in an extension direction of the detector, one end of the pressure measuring conduit being aligned with a surface of the detector in contact with the bottom surface of the tongue of the user.

In some embodiments, the other end of the pressure measuring conduit is connected to a pressure sensor, the pressure sensor being configured to determine a pressure between the detector and the tongue of the user.

In some embodiments, a wavelength of the light source signal emitted by the light source is within a range from 530 nm to 560 nm.

In an aspect of the present disclosure, a system for monitoring microcirculation is provided. The system may include a detector, the detector being inserted under a tongue of a user along a sagittal axis of the user; and a hook, the hook being hung on a tooth or a gum of the user for fixing the detector, wherein one end of the hook is optically coupled to a detection signal output terminal of the detector for receiving the detection signal, and a flexible optical fiber is disposed within the hook along an extension direction of the hook for transmitting the detection signal.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone) cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body. The term "an image of a subject" may be referred to as the subject for brevity.

For illustration purposes, the following description is provided to help better understanding an image registration process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

An aspect of the present disclosure relates to systems for monitoring microcirculation. A system for monitoring microcirculation may include: a detector, a light source, and a lens set located inside the detector. The detector is inserted under a tongue of a user in a sagittal direction of the user. The light source is disposed on a surface of the detector in contact with a bottom surface of the tongue of the user and is configured to emit a light source signal to a target area under the tongue. The lens set is disposed within the detector for receiving a detection signal from the target region, wherein the detection signal is emitted into the detector along a vertical axis direction of the user and emitted out from the detector along the sagittal axis direction of the user. The extension of the detector into the target region of the user in the sagittal axis direction of the user results in low pressure under the tongue, relieving pressures on small veins with thin vessel walls, and avoiding obstruction of blood flow in microcirculatory vessels. In some embodiments, the system for monitoring microcirculation may further include a hook connected to the detector. The hook being disposed on a tooth or a gum of the user to fix the detector. The hook makes the detector available for continuous and prolonged microcirculation monitoring under the tongue without being held by an operator. In some embodiments, the system for microcirculation monitoring may further include a processor to which the detection signal may be transmitted by wire (e.g., fiber optic) or wirelessly for microcirculation imaging.

The system for monitoring microcirculation may be configured in emergency departments (EDs), intensive care units (ICUs), and perioperative management in anesthesiology, etc. The microcirculation mainly includes a branching network of small arteries, capillaries, and small veins.

Figure 1:
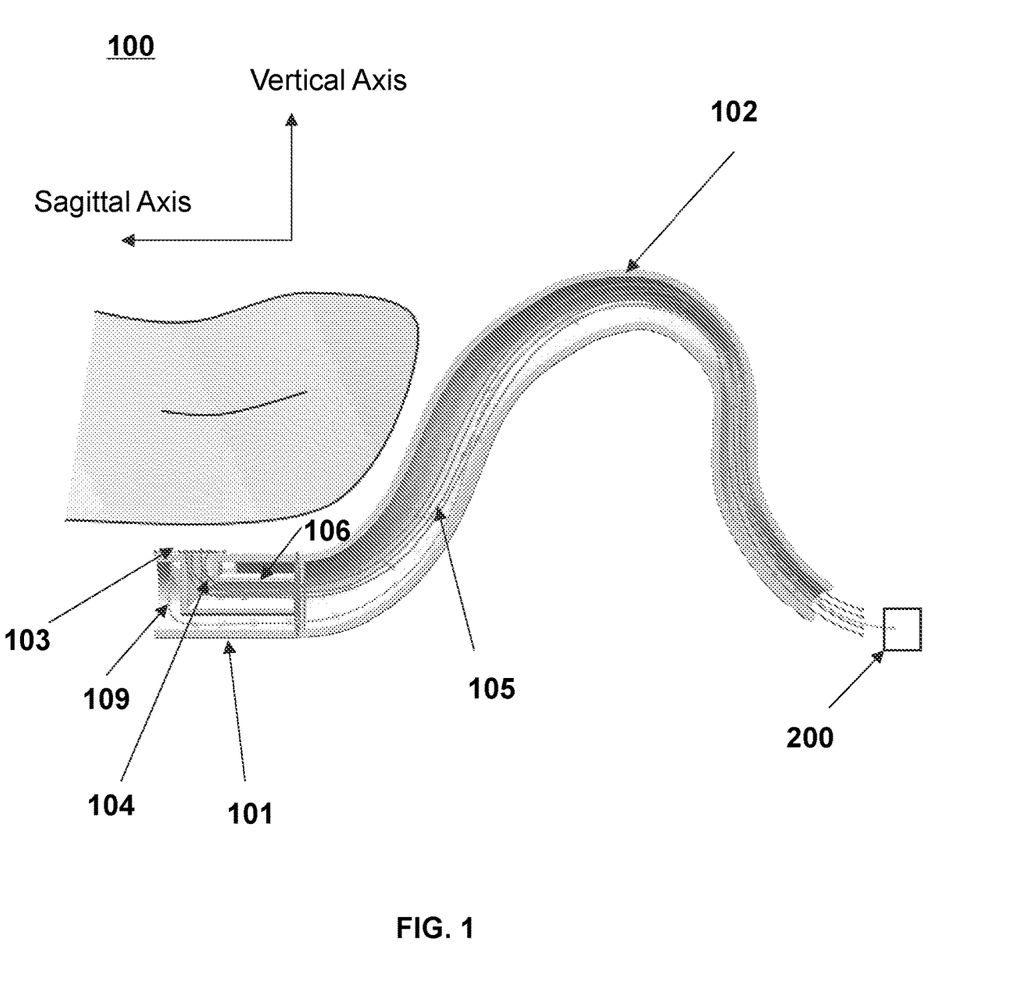
FIG. 1 is a schematic diagram illustrating an exemplary system for monitoring microcirculation according to some embodiments of the present disclosure.

FIG. 1 is a schematic diagram illustrating an exemplary system 100 for monitoring microcirculation according to some embodiments of the present disclosure.

As shown in FIG. 1, the system 100 may include a detector 101, a hook 102, a light source 103, a lens set 104, and a processor 200.

The detector 101 may be configured to detect microcirculation information of a target region in response to a light source signal emitted by the light source 103 to the target region, and generate a detection signal. As shown in FIG. 1, the detector 101 may be inserted under the tongue of the user along a sagittal axis direction of the user. In some embodiments, the detector 101 may form an accommodation space for accommodating the light source 103 and the lens set 104. For example, a surface of the detector 101 in contact with a bottom surface of the tongue of the user may be disposed with one or more holes for accommodating the light source 101. The one or more holes for accommodating the light source 101 may make the light source signal emitted by the light source 101 emit into the target region. In some embodiments, the accommodation space of the detector 101 may be made by 3D printing. A material of the detector 101 may include a resin polymer, a nylon, or the like, or any combination thereof. Descriptions regarding exemplary detector 101 may be found in FIG. 2 and the descriptions thereof.

In some embodiments, as shown in FIG. 1, the detector 101 may include an optical isolation zone 106 on a side of the detector 101. The side of the detector 101 may be near the surface of the detector 101 in contact with the bottom surface of the tongue of the user. The optical isolation zone 106 may be configured to block the light source signal or a reflected signal of the light source signal from emitting into the detector 101 and interfering with the detection signal. In some embodiments, the optical isolation zone 106 may be disposed inside the detector 101 near the light source 103.

In some embodiments, as shown in FIG. 1, the detector 101 further includes a pressure measuring conduit 109. The pressure measuring conduit 109 may be filled with liquid and disposed in an extension direction of the detector 101. In some embodiments, one end of the pressure measuring conduit 109 may be aligned with a surface of the detector 101 that is in contact with the bottom surface of the tongue of the user. The other end of the pressure measuring conduit 109 may be connected to a pressure sensor. The pressure sensor may be configured to determine a pressure between the detector 101 and the tongue of the user. Due to the incompressibility of the liquid, the liquid in the pressure measuring conduit 109 may transmit the pressure to the pressure sensor when the pressure between the detector 101 and the tongue of the user is great. In some embodiments, the pressure measuring conduit 109 may make it possible for the pressure sensor to monitor the pressure between the detector 101 and the tongue of the user in real time. The pressure measuring conduit 109 may also increase a contact area between the detector 101 and the tongue of the user.

The hook 102 may be configured to fix the detector 101 under the tongue of the user. In some embodiments, one end of the hook 102 may be connected to the detector 101, and a hooked portion of the hook 102 may be configured to locate the hook 102 on a tooth or a gum of the user. In some embodiments, one end of the hook 102 connected to the detector 101 may be optically coupled to a detection signal output terminal of the detector 101 (e.g., the end of the detector 101 connected to the hook 102 may be disposed with a fiber optic coupler) for receiving and transmitting the detection signal. For example, as shown in FIG. 1, an optical transmission channel (e.g., optical fiber 105) is disposed inside the hook 102 along the extension direction of the hook 102 for transmitting the detection signal. In some embodiments, in order to adapt to different mouth sizes or different teeth or gums of different users, a bending angle, a bending position, a bending depth, etc. of the hooked portion of the hook 102 may be adjusted according to the mouth sizes of the different users, and the detector 101 may be fixed under the tongue of the user. In some embodiments, in order to adapt to a hook-like bending structure of the hook 102 and make the bending angle, the bending position, and the bending depth of the hook portion adjustable, an external material of the hook 102 may be a flexible material, and the interior of the hook 102 may be disposed with a flexible optical fiber. In some embodiments, in order to obtain a high quality microcirculation image, the optical fiber 105 may be made of a material with a low filament breakage rate, a low dark filament rate, and a low string image rate. Descriptions regarding exemplary hook 102 mounted on the tooth of the user may be found in FIG. 3 and the descriptions thereof.

The light source 103 may be configured to emit a light source signal under the tongue of the user to illuminate the target region. In some embodiments, as shown in FIG. 1, the light source 103 may be disposed on the surface of the detector 101 in contact with the bottom surface of the tongue of the user. In some embodiments, the light source 103 may be disposed inside the detector 101 and transmit the light source signal to the target region through holes in the surface of the detector 101. In some embodiments, the light source 103 may be disposed within the holes in the surface of the detector 101 in contact with the bottom surface of the tongue of the user. The light source 103 may be apart from the surface of the detector 101 in contact with the bottom surface of the tongue of the user for providing the light source signal irradiated to the target region. In some embodiments, the light source 103 may emit a light source signal with a particular wavelength. Exemplary light source 103 may include a pulsed xenon arc light or lamp, a mercury arc light or lamp, a halogen light or lamp, a tungsten arc light or lamp, a laser, a laser diode, a light emitting diode, or the like, or any combination thereof. In some embodiments, the light source signal may be a coherent or a non-coherent light, and accordingly, the light source 103 may be a coherent light source or a non-coherent light source.

In some embodiments, the wavelength of the light source signal may be determined based on an absorption spectrum of hemoglobin and deoxyhemoglobin in the target region. For example, 420 nm (nanometers), 550 nm, and 800 nm are absorption peaks in the absorption spectra of hemoglobin and deoxyhemoglobin. Correspondingly, the light source 103 may emit a light source signal with a wavelength in the range from 530 nm to 560 nm. Exemplary wavelengths of the light source signal may include 530 nm, 540 nm, 550 nm, etc.

In some embodiments, the light source 103 may include at least one light source assembly. The surface of the detector 101 may be disposed with at least one hole for mounting the at least one light source assembly. In some embodiments, the light source signal emitted by the at least one light source assembly may be at an angle (e.g., 5°, 10°, 15°, etc.) to the bottom surface of the tongue of the user (i.e., the horizontal surface of the user) to emit the light source signal to the target region. In some embodiments, the angle at which the light source signal is emitted from the at least one light source assembly may be adjustable. For example, the operator of the detector 101 may adjust the angle of one or more of the light source assemblies to adjust an angle of incidence of the light source signal, and further to adapt to different oral cavity dimensions or different target regions under the tongue. In some embodiments, the light source 103 may include a light source component array distributed along a sagittal axis and/or a vertical axis of the user. In some embodiments, each light source component in the light source component array may be controlled to turn on or turn off for adapting to different oral cavity sizes or different target regions under the tongue. In some embodiments, the light source 103 may also include a light processing component that processes a light beam generated by at least one of the light source assemblies. Exemplary light processing component includes a convex lens for converging the generated light beam, a collimator for collimating the light beam, etc.

The lens set 104 may be configured to receive the detection signal from the target region such that the detection signal may be emitted into the detector 101 along the vertical axis direction of the user and emitted from the detector 101 along the sagittal axis direction of the user. In some embodiments, the lens set 104 may also be configured to focus the detection signal and eliminate color aberration. In some embodiments, the lens set 104 may be disposed within the accommodation space of the detector 101.

In some embodiments, the lens set 104 may include a microlens, a reflector, etc. The microlens may be configured to converge the detection signal of the target region and eliminate the color aberration. In some embodiments, a diameter of a spot of the converged detection signal of the microlens may be less than an inner diameter of the optical fiber 105 to reduce the loss of the detection signal. The reflector may be configured to make the detection signal emit into the detector 101 along the vertical axis of the user and emit from the detector 101 along the sagittal axis of the user. A central axis of the optical path in the detector 101 may be parallel to a bottom surface of the tongue (i.e., the central axis of the optical path may be parallel to the vertical axis of the user). Exemplary lens set 104 may be found in FIG. 2 and the descriptions thereof.

In some embodiments, the microlens may be designed according to the following equations. For example, a phase contour of the microlens may satisfy equation (1):

$$\varphi_{nf}(x, y) = \frac{2\pi}{\lambda_d}\left(f - \sqrt{x^2 + y^2 + f^2}\right), \tag{1}$$

where $\varphi_{nf}(x, y)$ denotes the phase contour, $\lambda_d$ denotes the wavelength of the light source signal, x and y denote position coordinates of each nanocell, and f denotes the focal length. The phase contour $\varphi_{nf}(x, y)$ may be obtained by rotating an angle $\theta_{nf}(x, y)$ at the given coordinates (x, y). Since $\varphi_{nf}(x, y) = 2\theta_{nf}(x, y)$, the rotation angle $\theta_{nf}(x, y)$ for each nanocell may satisfy equation (2):

$$\theta_{nf}(x, y) = \frac{\pi}{\lambda_d}\left(f - \sqrt{x^2 + y^2 + f^2}\right) \tag{2}$$

In some embodiments, the microlens may be a metasurface-based microlens. In some embodiments, the metasurface may be designed based on a birefringent nature of a single nanocell to function as a subwavelength half-wave sheet. By designing birefringence caused by asymmetric cross sections of reasonably length, width, and nano unit, the length, width, and height of each nano unit are fixed, and the rotation angle $\theta_{nf}(x, y)$ thereof may be determined according to equation (2).

In some embodiments, the thickness of the microlens may be in the range from 10 microns to 50 microns. For example, the thickness of the microlens may be about 30 microns. In some embodiments, the desired arbitrary phase distribution may be accurately obtained by designing the structure, size, and arrangement of the metasurface units at each position of the metasurface of the microlens.

In some embodiments, the microlens on the metasurface may include a metasurface unit array. The metasurface unit array may include a plurality of metasurface units. In some embodiments, the material, shape, etc., of the metasurface unit may be determined based on a phase compensation to achieve color elimination and convergence. For example, the metasurface unit array may include a plurality of media bins and/or media columns. For example, the metasurface unit array may include only media bins. Further, for example, the metasurface unit array may include only media columns. Further, for example, the metasurface unit array may include a combination of media bins and media columns. In some embodiments, the media columns and the media bins may be disposed in concentric circles in a staggered arrangement or in parallel rows and columns. In some embodiments, the media columns and media bins may be disposed irregularly as desired. Exemplary media columns may be a cylinder, a rectangular body, a prism, a cone, or the like, or any combination thereof. Exemplary media bins may be a cylindrical slotted structural body, a prismatic slotted structural body, a rectangular slotted structural body, or the like, or any combination thereof. In some embodiments, the metasurface unit array may be internally integrated with a battery resonance element. The battery resonance element may be configured to perform a phase compensation on the detection signal. In some embodiments, the material of the metasurface unit may include a gallium nitride that is transparent in the green light band. In some embodiments, when a numerical aperture of the microlens is 0.106 mm, the emitted parallel light may all converge to a same focal point in the green light band (e.g., with a focal length of 235 μm), thereby achieving color aberration elimination and focusing. In some embodiments, the efficiency of the microlens may exceed 40%. The quality of the microlens may be determined by determining whether the microlens approaches the diffraction limit $\lambda/2NA$, where $\lambda$ is the wavelength of the light source signal and NA denotes the numerical aperture.

The processor 200 may be configured to process the detection signal generated by the detector 101 and generate a microcirculation image of the target region based on the detection signal. For example, the processor 200 may extract vascular images from the microcirculation image based on neural networks. In some embodiments, as shown in FIG. 1, The processor 200 may be connected to the other end of the hook 102 away from the detector 101 for receiving and processing the detection signal generated by the detector 101. The processor 200 may generate the microcirculation image of the target region. In some embodiments, the processor 200 may be wirelessly connected to the detector 101. Exemplary processor 200 may be found in FIG. 4 and the descriptions thereof.

In some embodiments, the system 100 may include a sleeve. The sleeve may be configured to accommodate the detector 101. Exemplary sleeve may be found in FIGS. 5-6 of and the descriptions thereof.

It should be understood that connecting the detector 101 to the processor 200 via the hook 102 is only exemplary, and the detector 101 and the processor 200 may transmit the detection signal by other means. For example, the system 100 may only include the detector 101 and may not include the hook 102. The detector 101 may be fixed under the tongue of the user by other means (e.g., directly hold by the user under the tongue) and transmit the detection signal to the processor 200 by wireless means. As another example, the processor 200 may be integrated in the detector 101 for real-time processing of the detection signal and producing the microcirculation image. The processor 200 may transmit the microcirculation image or data of the microcirculation image, by wired or wireless means, to an external processing device or display device for further processing or display of the microcirculation image.

Figure 2:
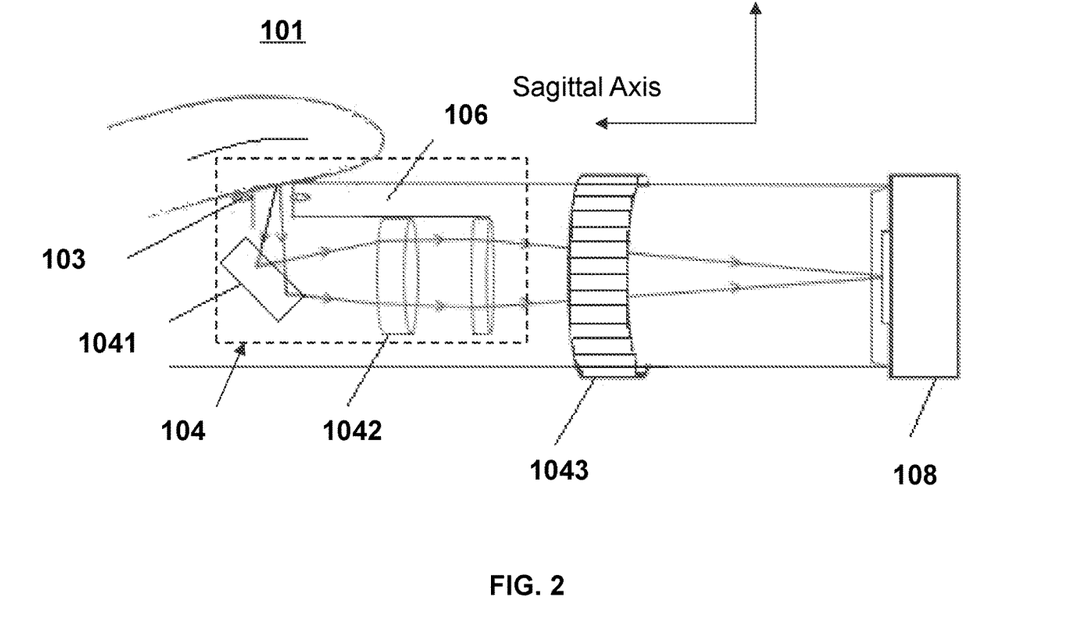
FIG. 2 is a schematic diagram illustrating an exemplary detector according to some embodiments of the present disclosure.

FIG. 2 is a schematic diagram illustrating an exemplary detector 101 according to some embodiments of the present disclosure.

As shown in FIG. 2, the detector 101 may include a light source 103, a lens set 104, a focusing assembly 1043, and a signal receiving end 108. The lens set 104 may include a microlens 1042 and a reflector 1041. During microcirculation monitoring, the detector 101 may be inserted under the tongue of the user in the sagittal axis direction of the user, and the light source 103 may light up the target region to provide the light source signal onto the target region. The light source signal may be scattered and absorbed internally by the target region and projected to the reflector 1041. The reflector 1041 may change the direction of the light path to achieve a 90° turn of the light path. The detection signal may be reflected by the reflector 1041 and projected onto the microlens 1042. The microlens 1042 may be configured to collect the scattered light under the tongue and achieve amplification of the detection signal. The detection signal may be amplified by the microlens 1042 and transmitted to the signal receiving end 108. In some embodiments, the signal receiving end 108 may be a fiber optic coupler that makes the detection signal transmitted to the processor 200 via an optical fiber (e.g., the optical fiber 105 as shown in FIG. 1). In some embodiments, in order to achieve accurate focusing of the blood vessels under the tongue, the focusing assembly 1043 may be disposed between the microlens 1042 and the signal receiving end 108 to focus the detection signal collected and amplified by the microlens 1042. Thus, the detection signal may be accurately transmitted to the signal receiving end 108.

It should be understood that the light path inside the detector 101 illustrated in FIG. 2 is only exemplary, and the light source 103, the lens set 104, and the signal receiving end 108 may be distributed in other light paths. For example, the light source signal, after being internally scattered and absorbed by the target region, may be projected to the microlens 1042 before being redirected by the reflector 1041.

Figure 3:
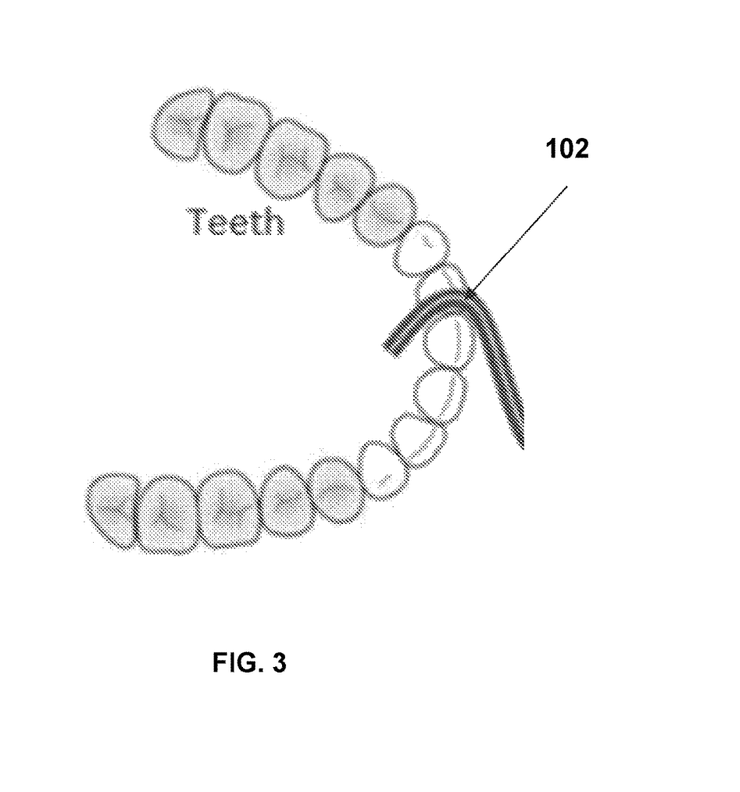
FIG. 3 is a schematic diagram illustrating an exemplary hook according to some embodiments of the present disclosure.

FIG. 3 is a schematic diagram illustrating an exemplary hook 102 according to some embodiments of the present disclosure.

In some embodiments, after the target region is determined, a tooth or a gum that is matched with the target region under the tongue may be determined. In some embodiments, a precise positioning of the target region may be achieved by the position of the tooth or gum matching with the target region. For example, a healthy adult may have 32 permanent teeth. The 32 permanent teeth may be divided into four regions: upper region, lower region, left region and right region, and divided into incisors, cusps, bicuspids (premolars), and molars according to tooth morphology and function, for a total of 16 pairs. Pairs of left and right teeth of a same name have a same anatomical form. For example, when a particular user performs a microcirculation monitoring under the tongue, the position of a particular cuspid for hooking the hook 102 may be recorded, and the position of the target region under the tongue for a previous detection may be easily informed when the next microcirculation monitoring under the tongue is performed. The likelihood of detecting the same target region under the tongue is great if it is hooked by the same cuspid. Thus, the tooth or gum may not only be configured to hold the detector 101, but also be configured for location marking. In some embodiments, when the elderly, for example, someone does not have teeth, a gum may be used for hooking the hook 102.

Figure 4:
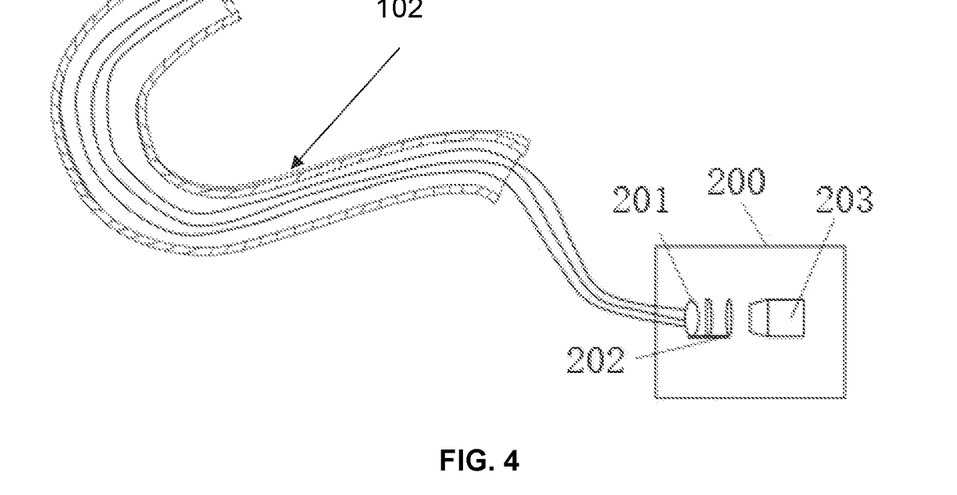
FIG. 4 is a schematic diagram illustrating an exemplary hook and an exemplary processor according to some embodiments of the present disclosure.

FIG. 4 is a schematic diagram illustrating an exemplary hook 102 and an exemplary processor 200 according to some embodiments of the present disclosure.

As shown in FIG. 4, the processor 200 may be connected to the end of the hook 102 away from the detector 101. The processor 200 may include an optical lens set 201, a motorized assembly 202, and an imaging array 203. In some embodiments, the optical lens set 201 may be configured to receive and amplify the detection signal transmitted by the optical fiber in the hook 102. The motorized assembly 202 may be configured to achieve an adjustment of focus and magnification. The imaging array 203 may be configured to perform a microcirculation imaging of the target region based on the detection signal to obtain a microcirculation image of the target region. In some embodiments, the processor 200 may also include a processing unit for processing the microcirculation image generated by the imaging array 203.

Figure 5:
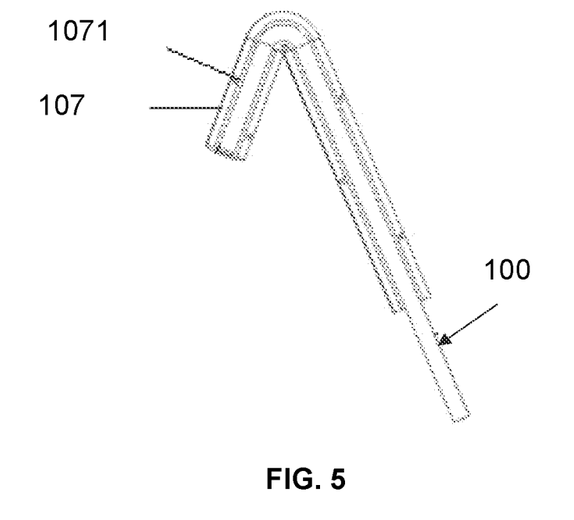
FIG. 5 is a schematic diagram illustrating an exemplary sleeve according to some embodiments of the present disclosure.

FIG. 5 is a schematic diagram illustrating an exemplary sleeve 107 according to some embodiments of the present disclosure.

In some embodiments, to improve the comfort of the under tongue contact of the user with the detector 101, the system 100 may further include a sleeve 107. In some embodiments, the sleeve 107 may be configured to accommodate the exterior of the detector 101 and/or the exterior of the contact portion of the hook 102 with the mouth of the user. In some embodiments, the shape of the sleeve 107 may match the shape of the detector 101 and/or the shape of the contact portion of the hook and the mouth of the user. In some embodiments, the surface of the sleeve 107 may be in the shape of a rounded curved surface of a bionic tongue.

In some embodiments, the sleeve 107 may have an open structure to facilitate the sleeve 104 to accommodate the detector 101 and/or the contact portion of the hook 102 with the mouth of the user. In some embodiments, as shown in FIG. 5, the sleeve 107 may be disposed with at least one snap-on structure 1071 for mounting or dismounting the sleeve 107.

Figure 6:
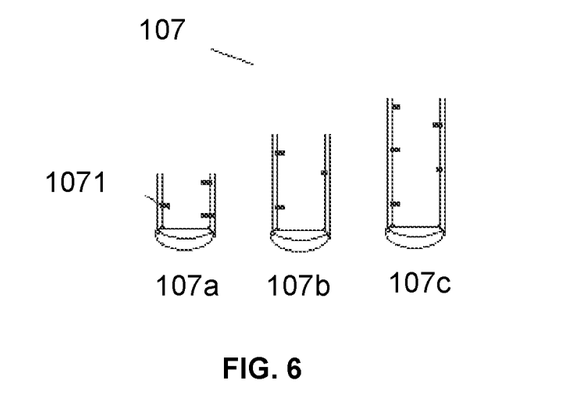
FIG. 6 is a schematic diagram illustrating an exemplary sleeve according to some embodiments of the present disclosure.

FIG. 6 is a schematic diagram illustrating an exemplary sleeve 107 according to some embodiments of the present disclosure.

In some embodiments, the sleeve 107 may involve different sizes for different users with different oral cavity sizes. As shown in FIG. 6, 107a shows a sleeve with a shorter length (e.g., 1.5 cm), which is inserted under a tongue of a child; 107b shows a sleeve with a medium length (e.g., 2 cm), which is inserted under a tongue of an adult woman; and 107c shows a sleeve with a longer length (e.g., 2.5 cm), which is inserted under the tongue of an adult man. As shown in FIG. 6, the at least one snap-on structure 1071 may be designed in different counts and positions depending on the different dimensions of the sleeve 107. For example, the longer the length of the sleeve 107 is, the greater the count of snap-on structures 1071 may be. Further, for example, the longer the length of the sleeve 107 is, the greater the distance between the plurality of snap-on structures 1071 may be.

Figure 7:
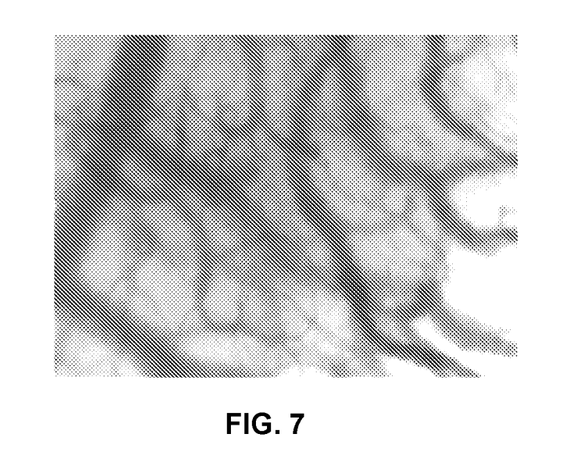
FIG. 7 is an exemplary microcirculation image according to some embodiments of the present disclosure.

FIG. 7 is an exemplary microcirculation image according to some embodiments of the present disclosure.

The target region under the tongue of the user was captured by the system 100 designed according to some embodiments of the present disclosure, and the microcirculation image is shown in FIG. 7. As shown in FIG. 7, the microcirculatory vessels in the target region under the tongue are clear.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system for monitoring microcirculation, comprising:
    a detector, the detector being inserted under a tongue of a user along a sagittal axis direction of the user, and the detector being placed parallel to the floor of the mouth of the user when the system is monitoring microcirculation;
    a light source configured to emit a light source signal to a target region under the tongue, the light source being disposed on a surface of the detector, the surface being in contact with a bottom surface of the tongue of the user and perpendicular to a vertical axis direction of the user, the surface being disposed with one or more holes for accommodating the light source;
    a lens set, the lens set being disposed within the detector for receiving a detection signal from the target region, wherein the lens set is configured that the detection signal is emitted into the detector along the vertical axis direction of the user and emitted out from the detector along the sagittal axis direction of the user, wherein the lens set includes a reflector and a microlens, wherein
        the reflector receives the detection signal from the target region and reflects the detection signal onto the microlens, wherein a direction of the detection signal transmitted from the target region to the reflector is perpendicular to the floor of the mouth of the user when the system is monitoring microcirculation;
        the microlens collects the detection signal from the reflector, amplifies the detection signal, and transmits the amplified detection signal to a signal receiving end, wherein a direction of the amplified detection signal transmitted from the microlens to the signal receiving end is parallel to the floor of the mouth of the user when the system is monitoring microcirculation.

2. The system for monitoring microcirculation of claim 1, further including: a hook connected to the detector, the hook being hung on a tooth or a gum of the user for fixing the detector, wherein a location of the target region under the tongue is determined by a position of the tooth or the gum on which the hook is hung.

3. The system for monitoring microcirculation of claim 2, wherein
    one end of the hook is optically coupled to a detection signal output terminal of the detector for receiving the detection signal; and
    a flexible optical fiber is disposed within the hook along an extension direction of the hook for transmitting the detection signal.

4. The system for monitoring microcirculation of claim 3, further including a processor, the processor being connected to the other end of the hook for receiving and processing the detection signal to generate a microcirculation image of the target region.

5. The system for monitoring microcirculation of claim 2, wherein a material of the hook is a flexible material.

6. The system for monitoring microcirculation of claim 1, further including a processor, the processor being wirelessly connected to the detector for receiving and processing the detection signal to generate a microcirculation image of the target region.

7. The system for monitoring microcirculation of claim 1, wherein the microlens is configured to converge the detection signal of the target region.

8. The system for monitoring microcirculation of claim 7, wherein the microlens is a metasurface-based microlens.

9. The system for monitoring microcirculation of claim 8, wherein the metasurface-based microlens includes a metasurface unit array, the metasurface unit array including a plurality of media bins or a plurality of media columns.

10. The system for monitoring microcirculation of claim 8, wherein the metasurface unit array is internally integrated with a battery resonance element for performing a phase compensation on the detection signal, and the battery resonance element is a material substrate to focus the detection signal to a focal point.

11. The system for monitoring microcirculation of claim 7, wherein the reflector is configured that the detection signal is emitted into the detector along a vertical axis direction of the user and emitted out of the detector along the sagittal axis direction of the user.

12. The system for monitoring microcirculation of claim 1, further including a sleeve for accommodating the detector.

13. The system for monitoring microcirculation of claim 12, wherein a shape of the sleeve is matched to a shape of the detector.

14. The system for monitoring microcirculation of claim 12, wherein a surface of the sleeve is a rounded curved surface of a bionic tongue.

15. The system for monitoring microcirculation of claim 12, wherein the sleeve is disposed with a snap-on structure for installing or removing the sleeve.

16. The system for monitoring microcirculation of claim 1, wherein the detector includes an optical isolation zone for blocking the light source signal or a reflected signal of the light source signal from emitting into the detector, the optical isolation zone is close to a side of the detector near the detector in contact with the bottom surface of the tongue.

17. The system for monitoring microcirculation of claim 1, further including a pressure measuring conduit, the pressure measuring conduit being filled with fluid and disposed in an extension direction of the detector, one end of the pressure measuring conduit being aligned with a surface of the detector in contact with the bottom surface of the tongue of the user.

18. The system for monitoring microcirculation of claim 17, wherein the other end of the pressure measuring conduit is connected to a pressure sensor, the pressure sensor being configured to determine a pressure between the detector and the tongue of the user.

19. The system for monitoring microcirculation of claim 1, wherein a wavelength of the light source signal emitted by the light source is within a range from 530 nm to 560 nm.

20. A system for monitoring microcirculation, comprising
a detector, the detector being inserted under a tongue of a user along a sagittal axis of the user, and the detector being placed parallel to the floor of the mouth of the user when the system is monitoring microcirculation;
a light source configured to emit a light source signal to a target region under the tongue, the light source being disposed on a surface of the detector, the surface being in contact with a bottom surface of the tongue of the user and perpendicular to a vertical axis direction of the user, the surface being disposed with one or more holes for accommodating the light source;
a lens set, the lens set being disposed within the detector for receiving a detection signal from the target region, wherein the lens set includes a reflector and a microlens, wherein
the reflector receives the detection signal from the target region and reflects the detection signal onto the microlens, wherein a direction of the detection signal transmitted from the target region to the reflector is perpendicular to the floor of the mouth of the user when the system is monitoring microcirculation;
the microlens collects the detection signal from the reflector, amplifies the detection signal, and transmits the amplified detection signal to a signal receiving end, wherein a direction of the amplified detection signal transmitted from the microlens to the signal receiving end is parallel to the floor of the mouth of the user when the system is monitoring microcirculation; and
a hook, the hook being hung on a tooth or a gum of the user for fixing the detector, wherein one end of the hook is optically coupled to a detection signal output terminal of the detector for receiving the detection signal, and a flexible optical fiber is disposed within the hook along an extension direction of the hook for transmitting the detection signal.

\* \* \* \* \*